(12) United States Patent
Siren et al.

(10) Patent No.: US 9,004,757 B2
(45) Date of Patent: Apr. 14, 2015

(54) SYSTEMS, ASSEMBLIES, COMPUTER READABLE MEDIA AND METHODS FOR MEDICAL IMAGING

(75) Inventors: Juuso Siren, Espoo (FI); Jari Taskinen, Tuusula (FI); Kaapo Paulanto, Nurmijärvi (FI); Tuomas Tölli, Vantaa (FI); Martti Kalke, Tuusula (FI)

(73) Assignee: PaloDEx Grou Oy, Tuusula (FI)

( * ) Notice: Subject to any disclaimer, the term of this patent is extended or adjusted under 35 U.S.C. 154(b) by 1078 days.

(21) Appl. No.: 12/730,867

(22) Filed: Mar. 24, 2010

(65) Prior Publication Data

US 2011/0235874 A1    Sep. 29, 2011

(51) Int. Cl.
| | | |
|---|---|---|
| *A61B 6/14* | (2006.01) | |
| *G03C 3/00* | (2006.01) | |
| *A61B 6/00* | (2006.01) | |
| *G03B 42/04* | (2006.01) | |

(52) U.S. Cl.
CPC . *G03C 3/003* (2013.01); *A61B 6/14* (2013.01); *A61B 6/4266* (2013.01); *A61B 6/5241* (2013.01); *G03B 42/042* (2013.01); *A61B 6/4423* (2013.01)

(58) Field of Classification Search
CPC ..................................................... A61B 6/145
USPC ........................................ 378/9, 38, 168–170
See application file for complete search history.

(56) References Cited

U.S. PATENT DOCUMENTS

| | | | | |
|---|---|---|---|---|
| 4,730,350 A | * | 3/1988 | Albert .............................. | 378/10 |
| 4,792,306 A | | 12/1988 | Duplantis | |
| 5,008,694 A | * | 4/1991 | Tajima et al. ................. | 396/518 |
| 5,274,691 A | * | 12/1993 | Neri .............................. | 378/183 |
| 5,388,140 A | * | 2/1995 | Robertson .................... | 378/187 |
| 5,446,779 A | * | 8/1995 | Ohta et al. .................... | 378/182 |
| 6,528,813 B2 | | 3/2003 | Yasuda | |
| 7,127,039 B2 | | 10/2006 | Woods | |

(Continued)

FOREIGN PATENT DOCUMENTS

| | | |
|---|---|---|
| JP | S58-118437 | 8/1983 |
| JP | 2000-258861 | 9/2000 |
| WO | 94/10605 | 5/1994 |

OTHER PUBLICATIONS

Brochure for "VistaScan", Durr Dental, www.vistascanperio.de. (Apr. 2006).

(Continued)

*Primary Examiner* — Hoon Song
(74) *Attorney, Agent, or Firm* — Andrus Intellectual Property Law, LLP (57) ABSTRACT

A medical imaging assembly includes a first imaging plate and a second imaging plate for acquiring a first and a second medical image. A container is configured to receive and hold the first imaging plate and the second imaging plate in a predetermined overlapping orientation. An image reader receives the first and second medical images and produces first and second digital medical images. A processor creates a composite image of the first and second digital images. A method of acquiring a medical image includes identifying an overlapped region of a lower image and an upper image. An alignment transformation is identified by matching the overlapped regions of the upper and lower images. The upper and lower images are aligned based upon the alignment transformation. A composite medical image is created from the upper image and the lower image.

36 Claims, 7 Drawing Sheets

(56) References Cited

U.S. PATENT DOCUMENTS

| | | | |
|---|---|---|---|
| 7,558,438 B1 | 7/2009 | Sasada | |
| 8,031,828 B1* | 10/2011 | DeMan et al. | 378/4 |
| 2002/0109102 A1* | 8/2002 | Steklenski et al. | 250/484.4 |
| 2003/0030721 A1* | 2/2003 | Nyholm | 348/36 |
| 2003/0048938 A1 | 3/2003 | Wang et al. | |
| 2004/0017888 A1* | 1/2004 | Seppi et al. | 378/57 |
| 2004/0071269 A1* | 4/2004 | Wang et al. | 378/174 |
| 2006/0233301 A1* | 10/2006 | Erhardt et al. | 378/38 |
| 2008/0019477 A1* | 1/2008 | Spartiotis et al. | 378/38 |
| 2008/0152088 A1 | 6/2008 | Wang et al. | |
| 2010/0034474 A1 | 2/2010 | Crucs | |
| 2010/0074402 A1* | 3/2010 | Bothorel et al. | 378/38 |
| 2010/0119036 A1* | 5/2010 | Muller | 378/38 |
| 2010/0232669 A1* | 9/2010 | Ziegler et al. | 382/132 |
| 2011/0069817 A1* | 3/2011 | Behle | 378/177 |

OTHER PUBLICATIONS

RCD Online Information for European Design Patent No. 001110506-0001, Registered Mar. 23, 2009; http://oami.europa.eu/RCDOnline/RequestManager?print=1, last visited Feb. 15, 2010 (2 pages).

RCD Online Information for European Design Patent No. 001110506-0002, Registered Mar. 23, 2009; http://oami.europa.eu/RCDOnline/RequestManager?print=1, last visited Feb. 15, 2010 (2 pages).

RCD Online Information for European Design Patent No. 001114201-0001, Registered Mar. 31, 2009; http://oami.europa.eu/RCDOnline/RequestManager?print=1, last visited Feb. 15, 2010 (2 pages).

IPDL Trademark Search Result; http://www.wipo.int/cgi-mad/guest/ifetch5?ENG+MADRID-FULL.vd . . . , last visited Feb. 15, 2010 (2 pages).

Makela, Tuomas, "Dental X-Ray Image Stitching Algorithm", Master's Thesis Submitted for Inspection in Espoo, Finland, on Oct. 2, 2009, Helsinki University of Technology.

Article Entitled "X-Rays and Intraoral Pictures", Colgate; http://www.colgate.com/app/Colgate/US/OC/Information/OralHealthBasics/CheckupsDentProc/XRays/XRaysandIntraoralPictures.cvsp, available Feb. 10, 2010 (7 pages).

Article Entitled Dental X-Rays, WebMD; http://www.webmd.com/oral-health/dental-x-rays, available Feb. 10, 2010 (2 pages).

Kennedy, Beverly J., RDH, MA, Abstract Entitled "Occlusal Film Exposures for the Child Patient", Contemporary Dental Assisting (Jul./Aug. 2007); http://www.dentalcareuniverse.com/index.php?ITEM=21068, available Feb. 10, 2010 (4 pages).

Dental X Rays Health Article, Healthline; http://www.healthline.com/galecontent/dental-x-rays, available Feb. 10, 2010 (4 pages).

Article Entitled "What Are X-Rays for Children at the Dentist Used for?", Health Development Advice; http://www.hda-online.org.uk/dentistry/x-ray/index.html, available Feb. 10, 2010 (5 pages).

Article Entitled "Dental X-Rays", Cosmetic Dentistry Guide; http://www.cosmeticdentistryguide.co.uk/articles/dental-x-ray.html, available Feb. 10, 2010 (4 pages).

Peterson, Dan, Dr., Article Entitled "Necessary Dental X-Rays", Family Gentle Dental Care; www.dentalgentlecare.com/necessary_x-rays.htm, available Feb. 10, 2010 (5 pages).

Japanese Office Action issued in corresponding JP Appn. No. 2010-86150 on Oct. 15, 2013.

* cited by examiner

SYSTEMS, ASSEMBLIES, COMPUTER READABLE MEDIA AND METHODS FOR MEDICAL IMAGING

FIELD

The present disclosure relates to medical imaging. More specifically, the present disclosure relates to systems, assemblies, computer readable media, and methods for medical imaging, for example intraoral medical imaging.

BACKGROUND

Imaging media for modern medical imaging can include film, reusable imaging plates, and/or wireless or wired x-ray sensors. Digital x-rays operate with imaging plate readers and with an assortment of imaging plates having different sizes.

SUMMARY

In one example, a medical imaging assembly includes a first imaging plate and a second imaging plate. A container is configured to receive and hold the first imaging plate and the second imaging plate in a predetermined overlapping orientation.

In another example, a system for medical imaging includes a first imaging plate for acquiring a first medical image and a second imaging plate for acquiring a second medical image. A container is configured to receive and hold the first imaging plate and the second imaging plate in a predetermined overlapping orientation during imaging. An image reader converts a first medical image of the first imaging plate and a second medical image of the second imaging plate to a first digital medical image and a second digital medical image. A processor receives the first and second digital medical images and creates a composite image of the first and second digital images.

In another example, a method of acquiring a medical image includes securing a lower imaging plate with an upper imaging plate in an overlapping orientation, applying radiation to the upper and lower imaging plates, reading a lower image from the lower imaging plate and reading an upper image from the upper image plate, identifying a border of an overlapped region of the lower image, aligning the lower image and the upper image, and creating a composite medical image by combining the aligned lower image and upper image.

In another example, computer readable medium is programmed with computer readable code that upon execution by a processor causes the processor to acquire a first image and a second image, orient the first image and second image in a general alignment, identify a lower image from the first image and the second image, identify a border of an overlapped region of the lower image, rotate the lower image to align the border of the overlapped region, match the lower image with the upper image, and combine the upper image and the lower image into a composite image.

DETAILED DESCRIPTION OF THE DRAWINGS

Figures 1A, 1B:
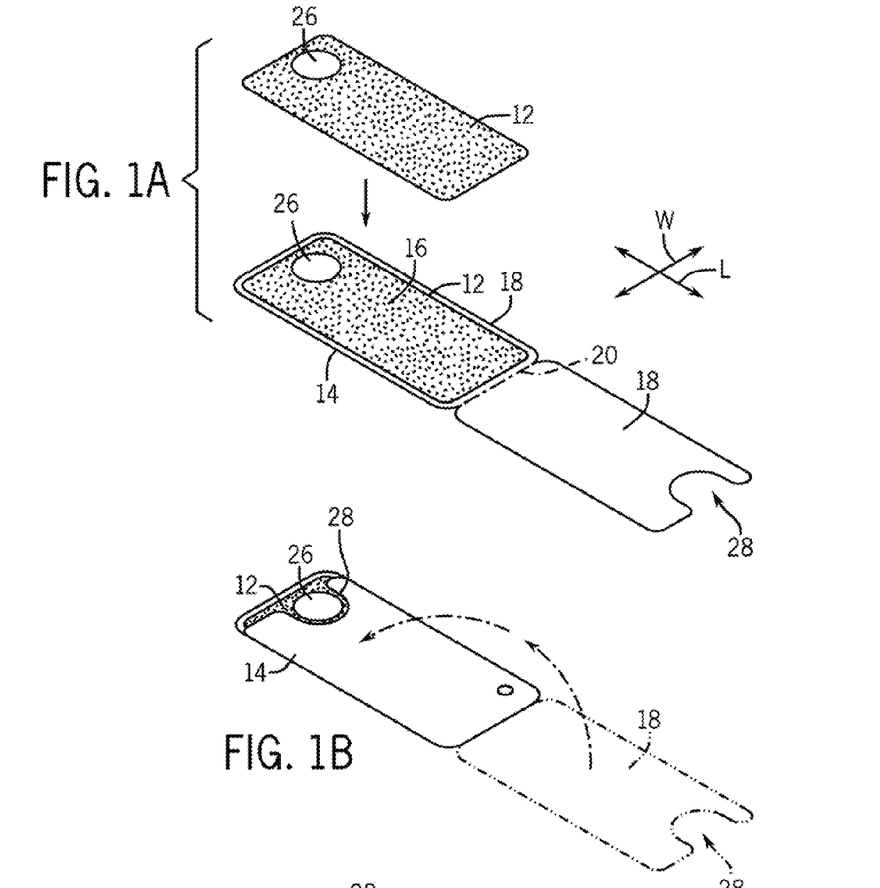
FIGS. 1A-I depict an embodiment of a medical imaging assembly.

FIGS. 1A-I depict components of one embodiment of a medical imaging assembly 10. FIG. 1A depicts an imaging plate 12 and a carton 14. The imaging plate 12 optionally includes a metal tab 26, which is used to align the imaging plate 12 with an image reader 54, as will be described herein below with reference to FIG. 2C. The imaging plate 12 is flexible, has a generally rectangular shape and rounded corners, and has elongated sides that extend in dimension L and relatively shortened sides that extend in dimension W, which is generally perpendicular to dimension L. Other geometric shapes and sizes of the imaging plate 12 can be used. In a preferred embodiment, the size of the imaging plate 12 is 70 millimeters×31 millimeters.

The imaging plate 12 includes a photostimulable phosphorous layer 16 that is capable of storing the energy of x-rays or other radiation. When stimulated by laser or other visible or infrared light, the phosphorous layer 16 emits light corresponding to an earlier absorbed energy. In the case of the phosphorous layer imaging plates 12, its earlier absorbed energy is x-ray energy from a medical imaging operation.

In one example, the imaging plate 12 can be used more than once. After an image has been read from the imaging plate 12, the imaging plate 12 can be "erased" by exposing the phosphorous layer 16 to, for example, a bright light. This releases any remaining absorbed energy and makes the imaging plate 12 ready to absorb x-ray energy in a subsequent medical imaging operation.

The carton 14, which use thereof may be optional, for example may be constructed of a resilient material, for example cardboard or the like, that protects the imaging plate 12. The carton 14 includes opposing sides 18 that are foldable towards each other about a seam or hinge 20. The carton 14 can be a unitary construction connected by the hinge 20 or a multi-part construction placed on the imaging plates 12 in segments. In use, the carton 14 protects the imaging plate 12. During assembly, the imaging plate 12 is placed on one side 18 of the carton 14 and then the other side 18 of the carton 14 is folded about the hinge 20 to cover the imaging plate 12. A cutout 28 in the carton 14 aligns with the tab 26, such that the tab 26 is exposed for interaction with the image reader 54, as will be described herein below with reference to FIG. 2C.

Figure 1C:
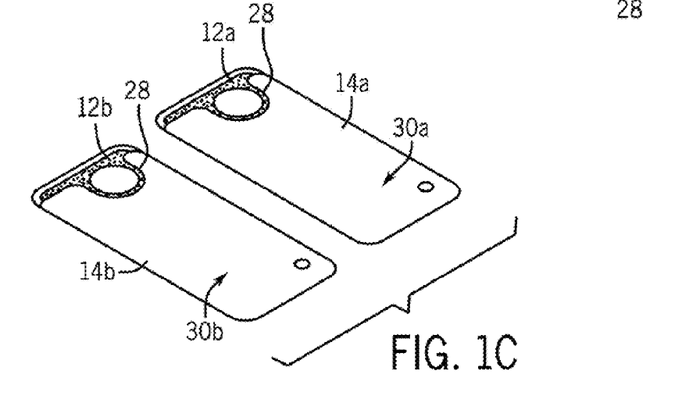

FIG. 1C depicts two imaging plate assemblies 30a and 30b, each including an imaging plate 12a, 12b, respectively, and a carton 14a, 14b, respectively, in accordance with the embodiments described above.

Figure 1D:
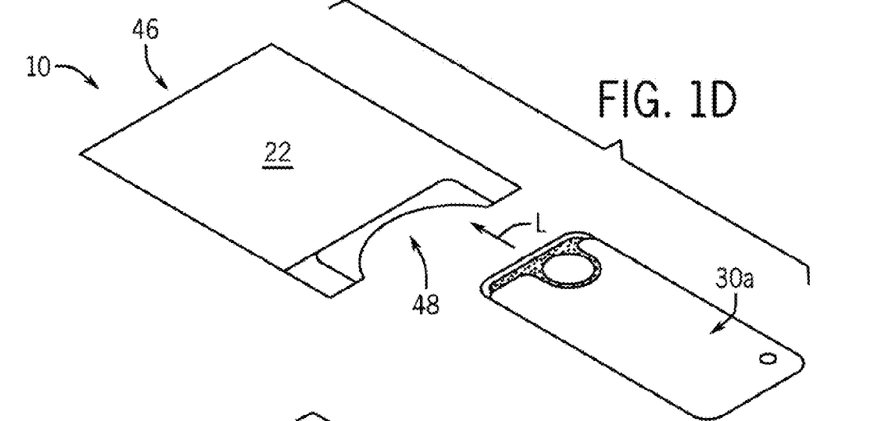

FIG. 1D depicts the first imaging plate assembly 30a being inserted into an optional container 22 in the dimension L. Alternative constructions of the container 22 may receive the imaging plates in an alternative orientation, for example through a side or through a bottom of the container 22. The container 22 protects each imaging plate 12a, 12b and also aligns the imaging plate assemblies 30a, 30b within certain predetermined alignment tolerances of each other, as will be described herein below. In the example shown, the container 22 holds the plates 12a, 12b and assemblies 30a, 30b in an overlapping orientation according to the alignment tolerances. The specific alignment and amount of the overlap between the two imaging plate assemblies 30a, 30b is predetermined to provide necessary data for image alignment, as well as to control the total imaging surface area provided by imaging plates 12a, 12b, as will be described further herein below.

The container 22 is rectangularly shaped and has a closed end 46 and an open end 48. Other shapes and sizes can be used. The container 22 can optionally be made of a carbon fiber, cardboard or any other suitable material identified by one skilled in the art. It is to be understood that some embodiments of the container 22 may be constructed in a reusable fashion, while other embodiments may be constructed for single use only. Design considerations regarding material and construction of the container may be determined based upon this intended use. Some embodiments of the container 22 can be constructed so as to protect the imaging plates from damage during acquisition of the medical image, or transport of the imaging plates before and after acquisition of the medical image.

Figure 1E:
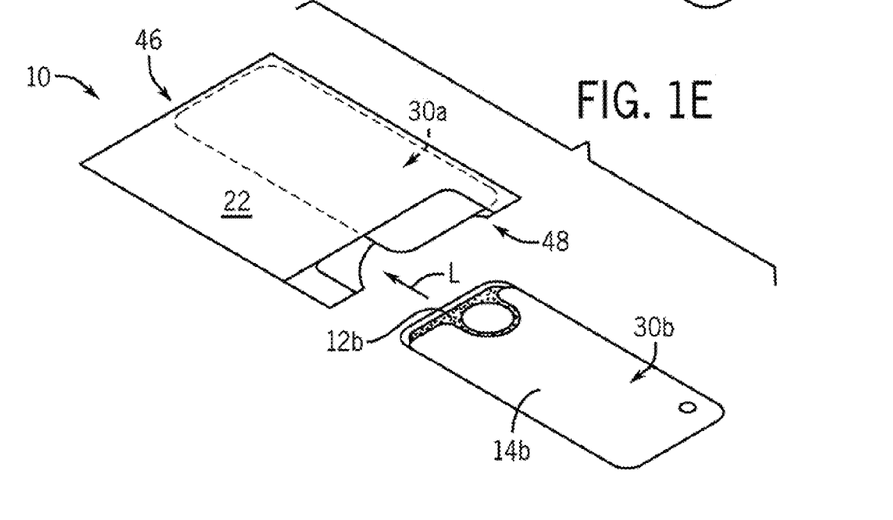

As shown in FIG. 1E, the imaging plate assemblies 30a, 30b are inserted into the container 22 via its open end 48. The container 22 is dimensioned so as to hold the imaging plate assemblies 30a, 30b by friction fit in the noted predetermined overlapping orientation. Alternatively, the container 22 may include one or more slots (not depicted) dimensioned to receive the imaging plate assemblies 30a, 30b in the predetermined overlapping orientation. Different containers 22 having different dimensions may be made available to a clinician such that a proper size of container 22 can be selected for the patient and imaging operation. The particular construction of the container 22 is not critical as long as it holds the imaging plate assemblies 30a, 30b in the noted predetermined overlapping orientation. While container 22 has been herein described as receiving two imaging plate assemblies, it is understood that in alternative embodiments, more than two imaging plate assemblies may be received within the container.

FIG. 1E depicts the placement of the second imaging plate assembly 30b into the container 22 in the length dimension L after the first imaging plate assembly 30a has been placed into the container 22. In embodiments of the medical imaging assembly 10, wherein the imaging plate assemblies 30a, 30b are secured in the container 22 by the interaction of the imaging plate assemblies 30a, 30b with the container 22, the carton 14 may be constructed of a resilient material, such that deformation of the carton 14 contributes to securing the imaging plate assemblies 30a, 30b in the container 22.

Figure 1F:
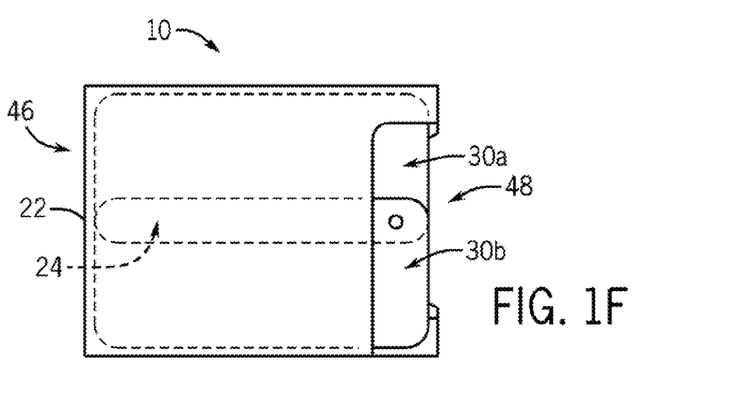

FIG. 1F depicts the first imaging plate assembly 30a and the second imaging plate assembly 30b held within the container 22. The first and second imaging plate assemblies 30a, 30b are arranged in the overlapping orientation and thus define an overlapped region 24. In a preferred embodiment, the alignment tolerance between the assemblies 30a, 30b is plus or minus 1 millimeter out of square in the dimension L and/or the dimension W for both of the imaging plate assemblies 30a, 30b. While the alignment tolerances may be larger or smaller than plus or minus 1 millimeter, the present inventors have found that this particular tolerance surprisingly strikes a suitable balance between manufacture and clinician operation precision and image processing demands. While the alignment tolerance may vary among embodiments, it is desirable for the tolerance to be known to thereby maximize image processing efficiency.

The systems and methods of this disclosure are not limited for use with the imaging plate media or media described above. Medical images may be acquired using other imaging media as well, including, but not limited to film and/or digital sensors and the like. The systems and methods are also not limited for use with the carton or the container described above. While the container can be a folder, it can be any structure that holds the imaging plate assemblies in an aligned and overlapped orientation. Alternative container structures, for example, a frame may be configured to receive imaging plate assemblies through the sides or bottom of the container. The size and construction of the container can be modified and tailored to achieve specified imaging surface areas and/or overlapping areas, when used in conjunction with imaging plate assemblies of standardized dimensions.

Figure 1G:
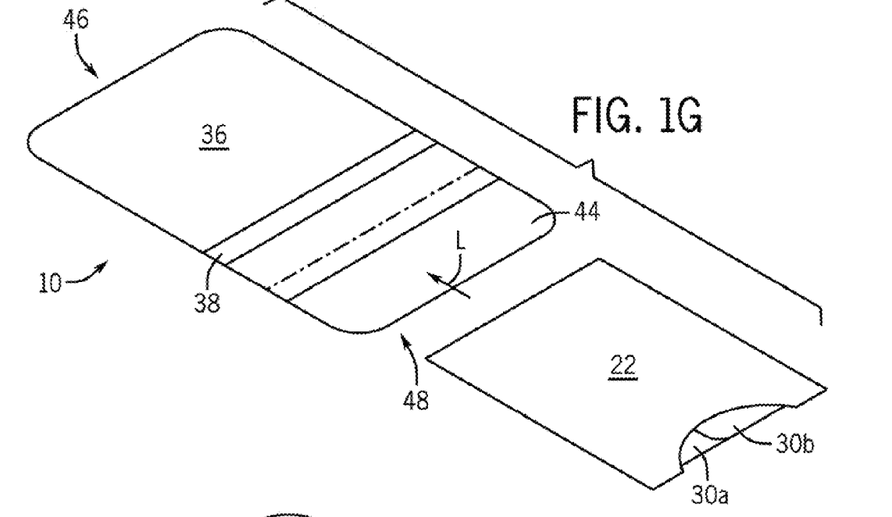
Figure 1H:
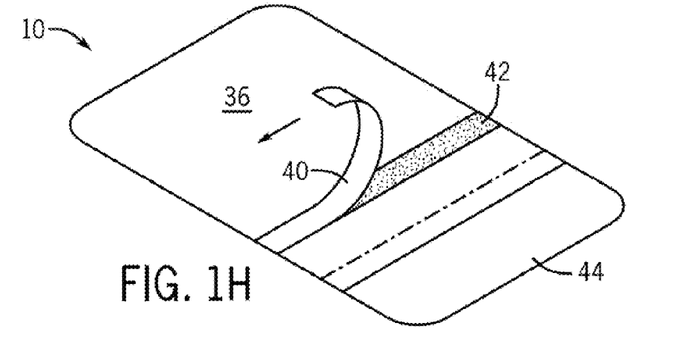
Figure 1I:
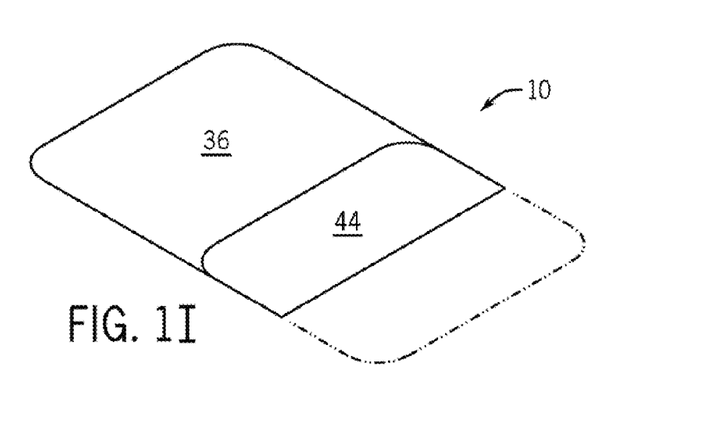

FIGS. 1G-1I depict placement of the container 22 and the imaging plate assemblies 30a, 30b into an optional hygienic pouch 36. The hygienic pouch 36 is, for example, made of a material compliant with ISO standard 10993-1 or the like to create a fluid impervious seal around the container 22 and imaging plate assemblies 30a, 30b. The hygienic pouch 36 preferably creates a liquid and biological barrier between the patient and the imaging plate assemblies 30a, 30b. This reduces contamination of the imaging plate assemblies 30a, 30b and prevents cross contamination when the imaging plates 12 are reused. The hygienic pouch 36 also serves to protect the container 22 and imaging plate assemblies 30a, 30b from exposure to fluid, which may damage these components and reduce the effective lifespan of reusable embodiments.

The hygienic pouch 36 optionally includes an adhesive strip 38 covered by a removable paper backing 40, which in use is peeled from the adhesive strip 38 to expose adhesive 42. The pouch 36 further optionally includes a foldable flap 44 that is moved into a closed position shown in 1I, thus sealing the hygienic pouch 36. Also, other examples of hygienic pouches that could be used with the presently described systems and assemblies are disclosed in International Patent Application Publication No. PCT/FI2009/051021, which is herein incorporated by reference in its entirety.

The following description herein refers to intraoral x-rays, and more specifically, occlusal x-rays; however, it is understood that alternative embodiments may be used or adapted for use in other medical imaging applications, and the disclosure specific references to intraoral and occlusal imaging are merely exemplary.

Figures 2A, 2B:
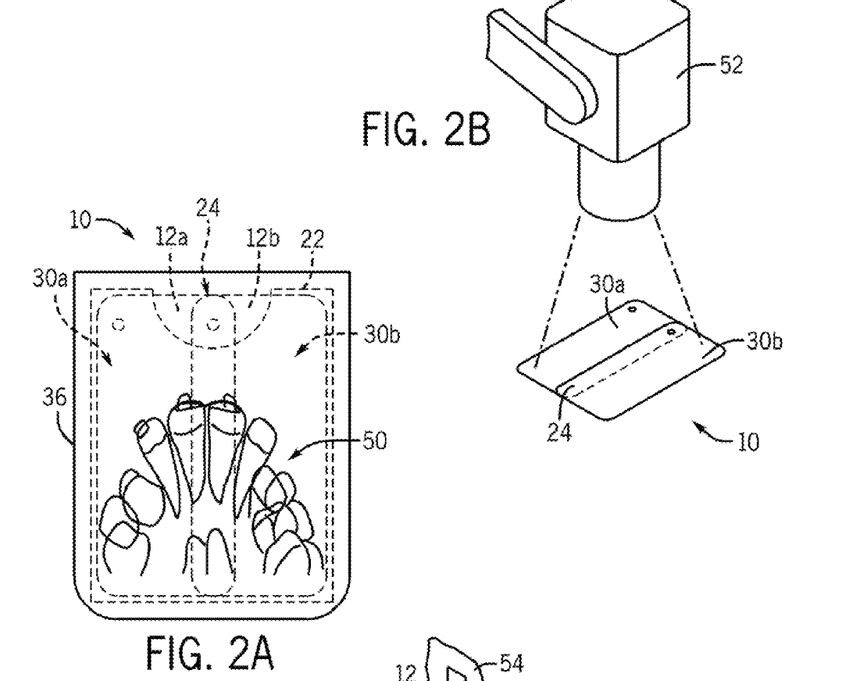
FIGS. 2A-C depict an embodiment of a system for acquiring and processing medical image data.
Figure 2C:
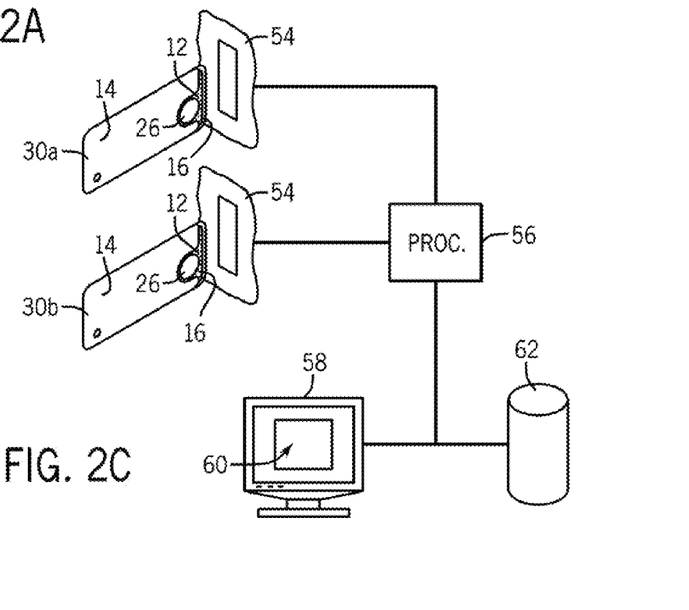

FIGS. 2A-2C depict an occlusal imaging system. Occlusal imaging is used to highlight tooth development and placement and is often used on children to identify how the primary and permanent teeth are developing. An additional use for occlusal imaging is in the diagnostic setting to investigate jaw fractures or suspected clefts in the pallet. An occlusal image usually depicts nearly the full arch of teeth in either the upper or lower jaw of the patient.

An example of an occlusal image is shown in FIG. 2A. According to one example of the present disclosure, the occlusal image is acquired by placing the assembly 10, including the imaging plates 12a, 12b, the container 22, and the hygienic pouch 36 between the biting surfaces of the patient's teeth. The container 22 protects the imaging plates 12a, 12b from crushing damage applied by the patient's bites. The hygienic pouch 36 prevents the spread of pathogens. The placement of an x-ray source with respect to the patient will determine the occlusal image that is obtained. If the x-ray source is placed over the nose of the patient, a maxillary occlusal image of patient's upper jaw will be obtained. If the x-ray source is placed under the chin of the patient, a mandibular occlusal image of the patient's lower jaw will be obtained.

FIG. 2A depicts an exemplary alignment of the patient's jaw 50 over the imaging assembly 10. The imaging assembly 10 includes the two imaging plate assemblies 30a and 30b arranged in an overlapping orientation within the container 22 and further disposed within the hygienic pouch 36. The overlapping orientation of imaging plate assemblies 30a and 30b define an overlapped region 24. The jaw 50 may be either the upper or the lower jaw of the patient, depending upon the orientation of the x-ray source, as described above.

FIG. 2B depicts irradiation of the imaging assembly 10 by a radiation source 52. One example of the radiation source may be the commercially available Instrumentarium FOCUS™ intraoral x-ray tube from PaloDEx Group Oy. With reference to FIG. 2C, after irradiation, the imaging plate assemblies 30a, 30b are removed from the hygienic pouch 36 and from the container 22 and then are transferred to an image reader 54 that acquires and digitizes the radiographic image recorded on each of the plates 12a, 12b. One example of a possible image reader 54 is that of the commercially available Soredex Digora® Optime reading device which is available from PaloDEx Group Oy. While FIG. 2C depicts the imaging plate assemblies 30a, 30b being read individually in parallel, it is understood that in an alternative embodiment, a single image reader 54 is used and the imaging plate assemblies 30a, 30b are read in series. In a still further example, multiple imaging plates may be read simultaneously by an image reader.

In use, an exemplary image reader 54 secures the imaging plate 12 to a sled (not depicted) with an electromagnetic interaction between the sled and the metallic tab 26 of the imaging plate 12. The sled moves the imaging plate 12 in a fixed direction. While the imaging plate 12 is moved, a laser beam (not depicted) sweeps across the imaging plate. When the laser hits the phosphorous layer 16, the phosphorous layer 16 emits a visible light with an energy that corresponds to the amount of x-ray radiation to which each location of the phosphorous layer was exposed. This emitted visible light is focused through a light amplifier tube (not depicted) and is then recorded by a light sensor (not depicted) into a digitized radiographic image. While this exemplary operation of the image reader is disclosed, it is understood that one of ordinary skill in the art would recognize that image readers of alternative construction and operation would also be suitable for use in systems disclosed herein.

The digitized radiographic images from the imaging plates are communicated to a processor 56 that performs image processing steps, as will be described in greater detail herein below, to take the separate radiographic images from each of the imaging plate assemblies 30a and 30b and convert them into a single composite image. The composite image is then provided to a graphical display 58 for visual presentation of a composite image 60. Alternatively, the composite image is provided to a database 62 for storage and later retrieval.

Figure 3:
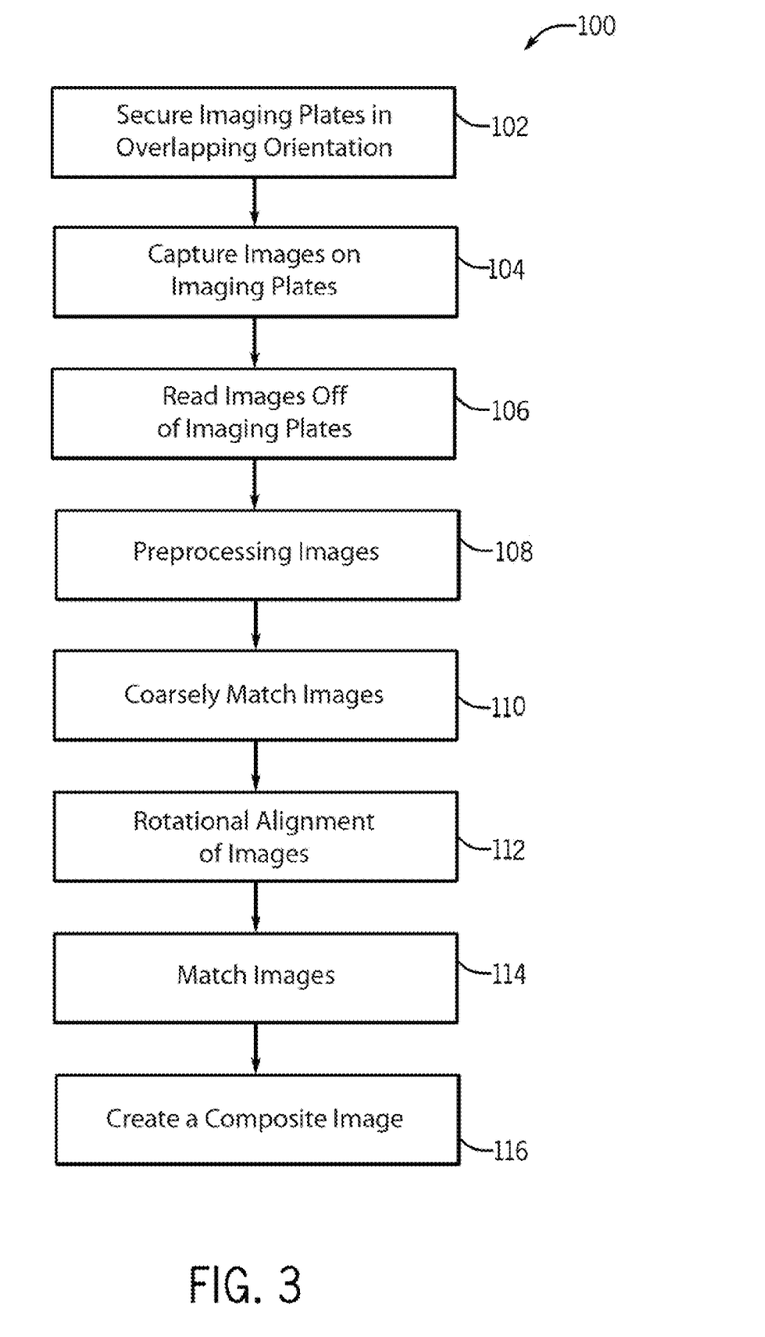
FIG. 3 is a flow chart depicting an embodiment of a method of acquiring a medical image.

FIG. 3 depicts an embodiment of a method 100 of acquiring a medical image. The method 100 will be described herein below with reference to the structures described above. It is noted that the embodiments of the method as specifically disclosed herein are merely exemplary of the processing that may be performed in the acquisition of a composite image. It is to be understood that alternative embodiments, not specifically disclosed herein, are within the contemplated scope of the disclosure and that the disclosed methods may be performed in alternative orders.

At 102, the first and second imaging plates 12a, 12b are secured in an overlapping orientation. As explained above, the first and second imaging plates 12a, 12b can be secured in the overlapping orientation for example by inserting the imaging plates 12a, 12b into the container 22. Additionally, a resilient property of the carton 14 may further enhance a friction fit between the imaging plates 12 and the container 22. As explained above, the carton 14 is optional and can be a unitary construction connected by a hinge or seam 20 or a multi-part construction placed on the imaging plates 12 in segments.

Figure 5:
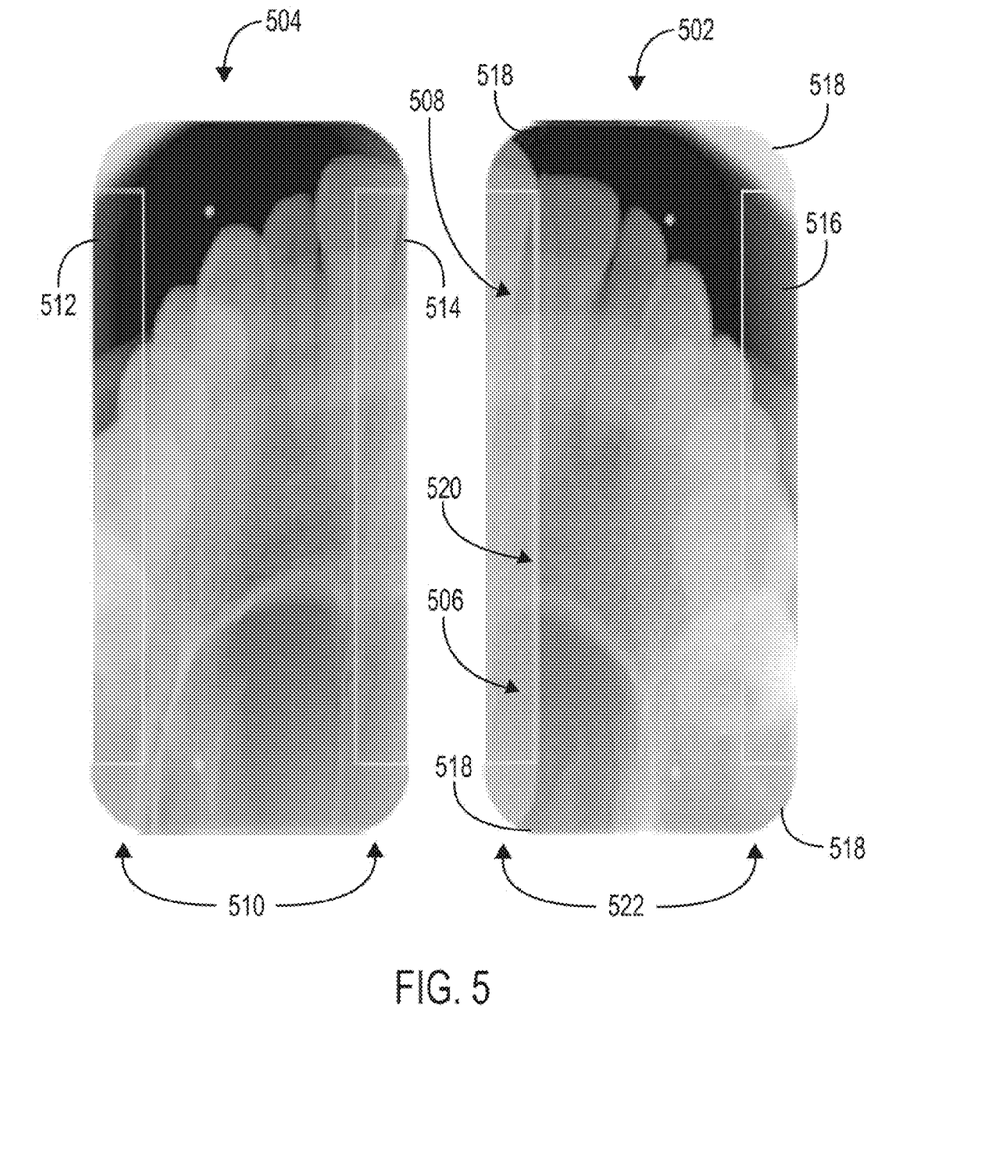
FIG. 5 depicts first and second medical images.

At 104, a first image and a second image are captured. FIG. 5 depicts an example of a first medical image 502 and a second medical image 504. The first medical image 502 and the second medical image 504 are captured at the same time by placing the overlapping first and second imaging plates 12a, 12b in the mouth of a patient and exposing the first and second imaging plates 12a, 12b to radiation such as from the x-ray radiation source 52 (see also FIGS. 2A and 2B). When radiation energy is passed through the jaw of the patient, it passes through soft tissue such as flesh and blood vessels. High density physiological structures such as bone, teeth, and fillings, absorb radiation and therefore cast radiographic "shadows" on the imaging plates. The phosphorous layer 16 of the imaging plates 12a, 12b absorb the varying levels of radiation and thus capture a radiographic image.

At 106, the first and second images are read off of the imaging plates 12a, 12b by the image reader 54. As described above, the image reader 54 produces digital medical images from the images captured on the first and second imaging plates 12a, 12b.

The, now digitized, first image 502 and second image 504 are provided to a processor that, at 108, preprocesses the first image 502 and the second image 504. Preprocessing at 108 includes coarsely aligning the first image and the second image. As noted above, the imaging plates are generally elongated in a length dimension L, and generally shortened in a width dimension W. Therefore, the corresponding first and second images acquired from these imaging plates have a similar rectangular shape. This shape is used to coarsely align the images such that the elongated length dimensions of the first image and the second image are arranged in parallel. FIG. 5 depicts an exemplary embodiment of this alignment.

Preprocessing at step 108 may optionally further include cropping of the image canvas around the first and second images. The first image and the second image typically include an image canvas that is larger than the actual image data. The image canvas is an artifact that results from the digitization process from the plate reader since the plate reader scans an area larger than the imaging plate in order to make sure all of the image data off of the imaging plate is acquired. Additionally, when the imaging plate is scanned, the image may not be squared on the image canvas. Therefore, the first image and the second image are both squared within their respective image files and the excess image canvas is cropped. In one embodiment, only the image canvas in the elongated length dimensions are cropped from the first and second images. This simplifies the cropping process while also reducing the risk that desirable image data is inadvertently removed from the first and second images. It is to be noted that this preprocessing is typically not performed when the entire medical image is acquired on a single plate. However, since the present method is directed to combining multiple images, this additional preprocessing is useful to remove sources of error for the forthcoming process.

At 110, the first image and the second image are coarsely matched. In FIG. 5, the first image 502 and the second image 504 are depicted in a proper alignment. However, it will be recognized by one of ordinary skill in the art that even after the coarse alignment performed above to place the first image 502 and the second image 504 in the same orientation, the first image 502 and the second image 504 may still be 180° out of alignment, or mirrored from proper alignment between the first image 502 and the second image 504. Therefore, at 110, one of the images is transformed, such as by rotation and/or mirroring in order to coarsely match the first image 502 and the second image 504.

At 112, the first image 502 and the second image 504 are rotationally aligned. In order to rotationally align the first image and the second image at 112, the first image 502 and the second image 504 must be identified as an upper image or a lower image, if this has not already yet been determined. Physical placement of the x-ray radiation source may be moved about the patient into different orientations. The terms "upper" and "lower" are used herein to describe the overlapped first and second imaging plates 12a, 12b and the images from these plates. In the present disclosure, "upper" is used to describe the image and the imaging plate that are closer to the radiation source, while "lower" is used to describe the image and the imaging plate that are further from the radiation source. Since the lower image was obtained from the lower imaging plate which was further from the radiation source, and therefore, at least partially behind the upper imaging plate in the overlapping orientation, a shadow 506 from the upper imaging plate appears in the lower image. This feature is used to initially identify the two images as the upper and lower images. In FIG. 5, the shadow 506 is found on the first medical image 502. Therefore, the first medical image 502 is the lower image and the second medical image 504 is the upper image.

The identification of the lower image 502 and the upper image 504 may be performed electronically by summing the grayscale values of all of the pixels in each column of both the first medical image 502 and the second medical image 504. Next, a rate of change between these summations is calculated. The lower image 502 will have the pixel column with the greatest rate of change between adjacent columns. This is due to the fact that the shadow cast by the upper imaging plate will produce an abnormally large change in total grayscale values in a predominantly vertical orientation. Once this discontinuity is identified, then that particular image is identified as the lower image 502.

After identifying the lower image 502 and the upper image 504, the lower image 502 is rotated such that the shadow 506 is placed in a vertical alignment. It has been noted that the imaging plates, and therefore the first and second images may be out of alignment, by a predetermined alignment tolerance when the imaging plates are placed in the overlapping orientation. Therefore, this misalignment may be corrected for by rotating the lower image 502 such that an interior border 520 of the shadow 506 is aligned in the vertical direction. With this vertical alignment of the side 508 of the shadow 506 in the lower image 502, the vertically oriented upper image 504 can be aligned with the lower image 502 by a translation comprising a vertical component and a horizontal component.

Once this rotational alignment of the lower image 502 and the upper image 504 is complete, overlapped regions of the lower image 502 and the upper image 504 are matched at 114. The matching may be generally described as determining a correlation between the overlapped regions of the lower image 502 and the upper image 504. Embodiments of the matching process will be described in greater detail herein; however, some embodiments of the matching include using a normalized mutual information method, as will be described in further detail herein, to calculate the correlation between the overlapped regions of the lower image 502 and the upper image 504. The goal of the matching of the overlapped regions of the lower image 502 and the upper region 504 is to identify a transformation that must be performed in order to align the overlapped region of the upper image 504 with the overlapped region of the lower image 502. Typically, the transformation comprises a spatial shift that includes a horizontal component and a vertical component.

In the currently described exemplary embodiment, the lower image 502 has already been rotated into an alignment orientation, and therefore the upper image 504 is spatially shifted in the matching process at 114. The matching of the overlapped regions of the lower image 502 and the upper image 504 iteratively compares the overlapped regions of the upper image 504 and the lower image 502 through a range of possible spatial shifts in order to identify the spatial shift that produces the best match between the overlapped regions of the lower image 502 and the upper image 504. While the transformation has herein been described as comprising a spatial shift of a horizontal and a vertical component, it is understood that in other embodiments, rotation, scaling, filtering, or other transformations may also be applied. However, in many embodiments, the imaging plates are thin compared to the distance between the imaging plates and the radiation source, the upper and lower images may be treated as co-planar, and therefore only the rotation of the lower image 502 and a spatial shift of the upper image 504 are needed to align the overlapped regions of the lower image 502 and the upper image 504.

Once the overlapped regions of the upper image 504 and the lower image 502 have been matched at 114, then a composite medical image is created at 116. The process of creating the composite medical image at 116 may be referred to as stitching as medical data from both the upper image 504 and the lower image 502 are combined to create the composite medical image.

Many different processing techniques may be used to select the image data used in the composite medical image. In one embodiment, the image data from the upper image 504 is selected for the composite medical image. Since the upper imaging plate casts a shadow 506 that is apparent in the lower image 502, it may be presumed that the image data of the upper image 504 in the overlapped region is of a higher quality. Alternatively, an analysis process may be established whereby image data from the upper image 504 may be rejected for including errors, or otherwise being deemed of a low quality. Such an event may occur if the phosphorous layer of the upper imaging plate was damaged along the overlapped region. This would produce detectable imaging errors in the overlapped region of the upper image 504. Upon such a detection, it may be desirable to alternatively select the image data from the overlapped region of the lower image 502, which may be of a higher quality.

In a still further embodiment, the overlapped regions of the lower image 502 and the upper image 504 are compared on a pixel-by-pixel basis. Each of these pixels are compared and the pixel of the higher quality is chosen for use in the composite medical image. The definition of quality of the signal data in each of the pixels may be determined based on a variety of factors and algorithms created to make this determination. In one embodiment, the pixel with the lower grayscale value is selected as the signal of higher quality. This is due to the fact that the more radiation that is absorbed by the imaging plate, the darker (and therefore lower) the signal data will be at that pixel. Since overlapped or damaged portions of the imaging plate will reduce the plate's ability to absorb radiation at the damaged portions, the darker image (corresponding to lower grayscale value) can be assumed to be the image data of high quality.

Figure 4:
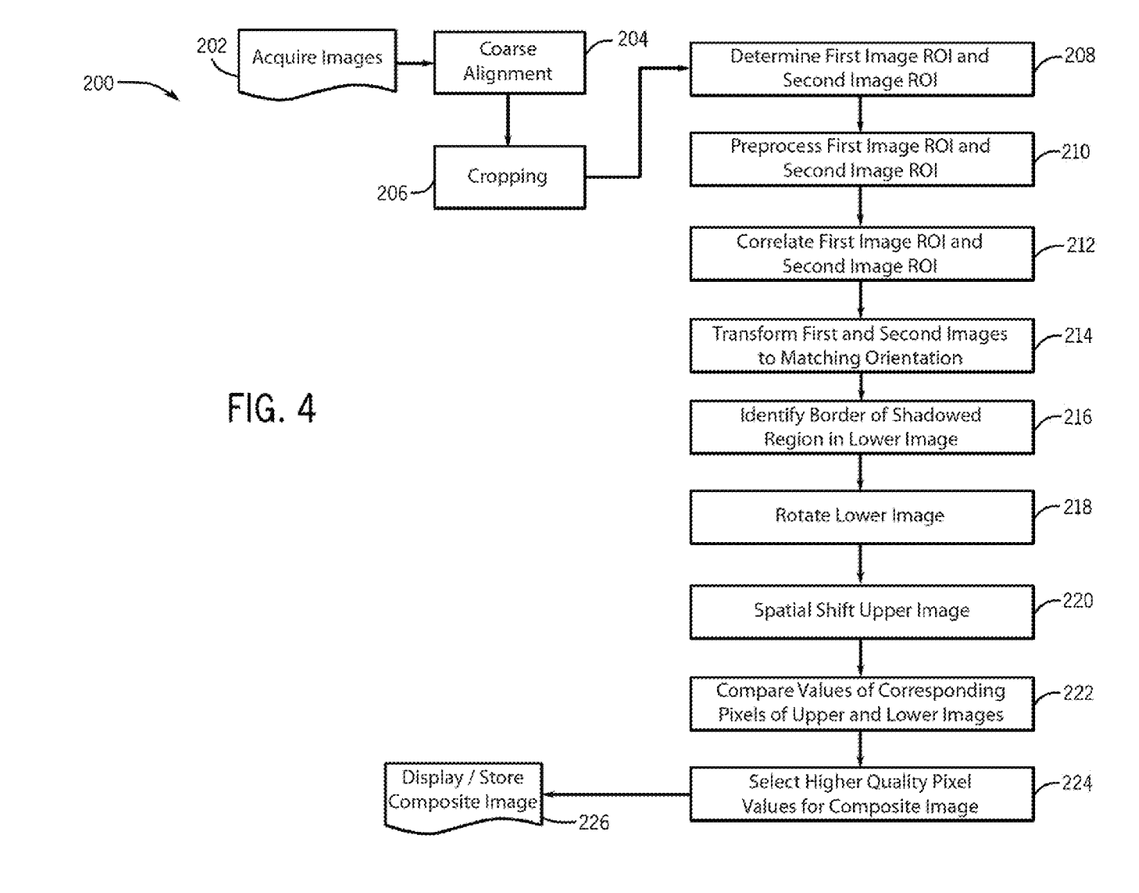
FIG. 4 is a flow chart depicting another embodiment of a method of acquiring a medical image.

As stated above, FIG. 4 depicts a flow chart of a method 200 that may be performed by a computer processor 56 (FIG. 2c) by executing computer readable code stored on a computer readable medium. Additionally, the method 200 will address in greater detail some of the signal processing steps that may be performed in embodiments of the method 100 (FIG. 3).

Referring to FIG. 4 and FIG. 5, a first image 502 and a second image 504 are acquired at 202. The first image 502 and the second image 504 are digital images that may be acquired from an image reader such as has been described above. However, the first image 502 and the second image 504 may be alternatively acquired from any other source of digital images, including previously recorded and stored digital images.

The first image 502 and the second image 504 are coarsely aligned at 204. Since the first image 502 and the second image 504 are generally rectangular, the first image 502 and/or the second image 504 may be rotated into the same general orientation as depicted in FIG. 5. This exemplary orientation with the first image 502 in parallel with the second image 504 will be used in the forthcoming description; however, it is understood that other orientations, for example a horizontal alignment may be used.

Next, at 206, the first image 502 and the second image 504 are rotated on their respective image canvases (not depicted) in order to square the images, and cropped to remove some or all of the image canvas. The first medical image 502 and the second medical image 504 will typically include an image canvas (not depicted) that is larger than the actual image data. The image canvas is an artifact that results from the digitization process since the image plate reader scans an area larger than the image data in order to make sure all of the image data is acquired. Additionally, when an imaging plate is scanned, the image may not be squared on the image canvas. Therefore, the image must both be squared within the image file and the excess image canvas cropped off.

The image canvas may be identified by an analysis of a histogram in order to determine a cutoff grayscale value that will eliminate the unused image canvas (which appears as white image data) from the desired image data.

This preprocessing is often not performed when the entire medical image is acquired on a single plate. However, since the present method is directed to combining multiple images, this additional preprocessing is useful to remove sources of error for the forthcoming process. In an embodiment, only the image canvas from the sides of the images in the elongated lengthwise dimension are cropped. This is done to minimize the processing required for cropping as well as to minimize the potential for data loss due to the cropping. While cropping has been herein described as occurring during the preprocessing, it is understood that in alternative embodiments, cropping may be performed at other stages in the method.

Since it is known that only a portion of the first image 502 and the second image 504 overlap, in some embodiments the signal processing is simplified by selecting a region of interest (ROI) window from the first image and an ROI window from the second image, for example, as described herein at 208.

ROI windows are chosen from both sides of the first image 502. A first ROI window 508 is chosen from one side 522 of the first image 502 and a second ROI window 516 is selected from the other side 522 of the first image 502. Since it is known that the overlapped region occurs on one of the sides 522 of the first image 502, the first ROI window 508 and second ROI window 516 of the first image 502 may be selected as a comparatively thin strip of data along one of the sides 522 of the first image 502. In one exemplary embodiment, the first ROI window 508 and the second ROI window 516 each comprise 10% of the width of the first image 502; however, this is merely exemplary and contemplated embodiments of the first and second ROI windows may include more or less of the image data. The first and second ROI windows may further exclude data from the corners 518 of the first image 502. This may help to eliminate errors and/or discontinuities in the image data due to the shape of the imaging plate. In a merely exemplary embodiment, the dimensions of the first ROI window 508 and the second ROI window 516 are identical such as to facilitate signal processing as will be described further herein.

The identification of the second image ROI window requires additional signal processing. The generally rectangular shapes of the lower image 502 and the upper image 504 allow for the coarse alignment performed at 204. However, the overlapped region of the upper image may be on either side 510 of the upper image 504 as the upper image 504 may be 180° out of alignment with the lower image 502. Alternatively, the upper image 504 may be mirrored from the lower image 502. A first ROI window 512 of the second image 504 is defined from one side 510 of the second image 504 and a second ROI window 514 is defined from the opposite side 510 of the second image 504. The first ROI window 512 and the second ROI window 514 of the second image 504 also have the same dimensions as the first ROI window 508 and the second ROI window of the first image 502.

After the ROT windows 508, 512, 514, and 516 are determined at 208, the ROI windows 508, 512, 514, and 516 are preprocessed at 210. This preprocessing normalizes the color values across the first and second ROI windows 508, 516 of the first image 502 and the first and second ROI windows 512, 514 of the second image 504. Additionally, the color depth of the first and second ROI windows 508, 516 and the first and second ROI windows 512, 514 may be reduced. As an example, images acquired with a Soredex Digora® Optime plate reading device, are stored with a color depth of 14 bits corresponding to 16,384 different grey levels per pixel. Therefore, the color depth ROI windows 508, 512, 514, and 516 may be reduced. This can be done to simplify the complexity of the processing, without eliminating data necessary to coarsely match the images.

The first and second ROI windows 508, 516 compared at 212 to the various possible orientations (including mirroring) of the first and second ROI windows 512, 514 of the second image 504. An image registration process may be performed to coarsely match the first image 502 and the second image 504. Image registration is a process where two or more images are transformed in a geometrical manner so that the coordinates of the images become parallel and the images can be matched. In an embodiment, this comparison may be made using a mutual information method, which will be described in further detail herein. In an alternative embodiment, image intensity is used. Generally, this comparison produces a measurement of the correlation between the first ROI window 508 and the first and second ROI windows 512, 514 of the second image. The comparison further produces a measurement of the correlation between the second ROI window 516 and the first and second ROT window 512, 514 of the second image. The combination of the ROI window (508, 516) of the first image 502 and the ROI window (512, 514) of the second image 504 that are determined to be the best match, such as by the mutual information method, are selected as the first image ROI window and the second image ROI window. In FIG. 5, the first ROI window 508 of the first image 502 is selected as the first image ROI window and the second ROI window 514 of the second image 504 is selected as the second image ROI window. At 214, the first and second images are transformed to a matching orientation. In the coarse alignment at 204, the first image 502 and the second image 504 were arranged in a generally parallel orientation. The second image 504 can be identified, in the correlation at 212, as either 180° out of alignment or mirrored from the first image 502. If this is the case, then the second image 504 is transformed to coarsely match the first image 502 with the second image 504. This transformation in 214 may exemplarily include a rotation or a mirror; however, other transformations are also contemplated.

At 216, the first image 502 and the second image 504 are analyzed in order to identify a border of a shadowed region of a lower image. Since the first image 502 and the second image 504 are acquired from radiation absorbent imaging plates arranged in an overlapping orientation, the imaging plate that is closer to the radiation source will cast a shadow that will be apparent in the lower image.

The upper image and the lower image may be determined by identifying which of the first image 502 and second image 504 includes an area of higher grayscale pixel values (corresponding to the shadow 506) in the image than is expected and, in particular, a border of that area. In order to make this determination, the grayscale pixel values for each column of data in both the first image 502 and the second image 504 are summed. This summation series is differentiated to determine the change in the grayscale pixel value summation between adjacent columns. A maximum peak can be identified in the differentiation. This peak coincides with a border 520 of the overlapped region 506 on the lower image. Thus, the image of the first image 502 and the second image 504 that exhibits the maximized differentiation peak is the lower image 502 and the other of the first and second images is the upper image 504. However, it is understood that the upper and lower images may be identified in other ways, including by clinician observation and manual input. Since the first image ROI window 508 and the second image ROI window 514 have already been identified, these ROI windows may be used to simplify this signal processing, as the border 520 is already known to be approximately in the area of an interior edge of the first image ROI window 506 and the second image ROI window 514.

When the border 520 of the overlapped region 506 is identified, then at 218 the lower image 502 is rotated until the border 520 is aligned with a vertical axis. As described above with respect to FIGS. 1 and 3, the imaging plates may be held in the overlapping orientation within a predetermined alignment tolerance. In order to correct the upper image 504 and lower image 502 for any misalignments within the alignment tolerance, the lower image is rotated as described. By rotating the lower image 502 until the border 520 of the overlapped region 506 is vertically aligned, then the first image ROI window 508 will match the second image ROI window 514 with a translation, which may include a horizontal component and a vertical component.

As noted above with respect to FIG. 1, the container 22 may be constructed such that it secures the imaging plates 12 within a predetermined alignment tolerance. In an exemplary embodiment, the predetermined alignment tolerance may be one millimeter out of square in any direction for both of the imaging plates 12. The predetermined alignment tolerance provides two noted features. First, by building an alignment tolerance into the container 22, the container 22, the acquisition of the images is made easier for a technician as the technician can be less concerned with establishing an exactly squared alignment between the imaging plates. Additionally, when the image processing is performed to align the first image with the second image, a maximum rotation angle may be calculated from the geometric dimension of the imaging plates and the predetermined alignment tolerance. This maximum rotation angle range reduces the possible rotation angle through which the lower image must be rotated in the above process. By restricting the angles by which the lower image may be rotated, the required signal processing is reduced and the computations may be performed more efficiently.

As an exemplary embodiment, the imaging plate has previously been described as having dimensions of 70 mm×31 mm. In the above described alignment tolerance, the largest angle is produced when both ends of the plate move 1 mm in opposite directions, which means that the maximum alignment angle can be calculated from the triangle with these dimensions. Therefore, the lower image 502 need only be rotated through plus and minus this calculated rotation angle in order to vertically align the border 520 of the overlapped region 506.

After the lower image 502 has been rotated at 218, the upper image 504 is translated at 220 by a vertical component and a horizontal component to finely match the lower image 502. The alignment of the upper image 504 with the rotated lower image 502 may be performed using a variety of techniques or methods for calculating correlation between two images or data sets. The exemplary embodiment described herein will be described as using the normalized mutual information method (NMI) which is an area based image registration method.

The mutual information method measures the entropy or uncertainty between two data sets. In the mutual information method, two images are moved, rotated, scaled, or otherwise transformed in more sophisticated ways in order to find the combination of transformations to the two images that produce the best match between the images. Whereas entropy measures the randomness in one set of information, joint entropy calculates the randomness between two sets of data or images.

Since entropy is a measure of uncertainty in a signal, and we want to identify the conditions upon which the two images match, the joint entropy must be related back to the entropies of the two original images. This is the mutual information measure which is represented by the equation:

$$NMI(A, B) = \frac{H(A) + H(B)}{H(A, B)}$$

In the above equation, H(A) and H(B) are the entropies of the separate lower image ROI window and the upper image ROI window and H(A,B) is the joint entropy between the lower image ROI window and the upper image ROI window.

The mutual information method is implemented at 220 to find a spatial shift including a vertical component and a horizontal component that is required to align the overlapped regions of the upper image 504 and the rotated lower image 502. This is achieved by performing the following loops through possible spatial shift combinations of vertical and horizontal translations. The upper image ROT window 514 is moved through possible spatial shifts that align an edge of the upper image 504 with the border 520 of the lower image 502. The spatial shifts comprise a coordinate pair, including a vertical component and a horizontal component. As noted above, since the imaging plates that are used to acquire the first image and the second image are thin, with respect to the distance of the imaging plates from the radiation source, the first image and the second image can be considered to be in the same image plane with respect to each other. This simplifies the image registration process as the images only need to be rotated (at 216) and shifted (at 220) within the same plane in order to align the upper and lower images. However, it is understood that in alternative embodiments, more complex transformations may be required.

The mutual information value is calculated between overlapping portions of the lower image and the upper image for each of the possible spatial shift of the upper image 504 across the lower image 502. The newly calculated mutual information value is compared to a previously determined maximum mutual information value. If the new mutual information value is higher than the previous maximum, then the vertical component and the horizontal component of the spatial shift resulting in the new maximum mutual information value are stored in the processor memory.

After the upper image 504 has been aligned with the lower image 504, the upper and lower images are combined.

The combining process in one embodiment is the simple selection of the image data from the upper image 504 for all portions of overlapping data. In generalized embodiments, this can be done since the overlapped region 506 of the lower image 502 includes the shadow from the upper imaging plate. Therefore, in most instances, the image data from the upper image 504 will be of a higher quality than the image data from the lower image 502 in the overlapped region 506.

In alternative embodiments, additional signal processing may be used to select between the image data of the upper image 504 and the lower image 502 in the overlapped region. Such signal processing may be used to identify errors in the image data of the upper image 504 in the overlapped area at which point the upper image data would be rejected in favor of selecting the lower image data. Such errors in the overlapped region of the upper image 504 may occur from a damaged imaging plate, or damaged phosphorous on the imaging plate, such as caused by a scratch. An alternative example of an error includes that resulting from an imaging plate identification mark. Such an imaging plate identification mark may include alphanumerical characters, symbols, or a bar code that is apparent in the images obtained by that imaging plate. The imaging plate identification mark is unique to the imaging plate and therefore the imaging plate may be cross referenced to the images that it captures. These imaging plate identification marks can effectively block a portion of image data. Therefore, if an imaging plate identification mark is present in the overlapped region between the upper and lower plates, then the image data from the upper or lower image that does not contain the imaging plate identification mark, may be used in the composite image.

At 222, the combining process is performed by comparing the values of corresponding pixels of the overlapped regions of the upper and lower images. In this embodiment, the overlapped regions of the aligned lower image 502 and the upper image 504 are separated into corresponding pairs. These pairs of pixel values are compared in order to identify the higher quality pixel value. In one embodiment, the higher quality pixel value is the lower grayscale pixel value. Since the imaging plates absorb radiation and the greater amount of absorbed radiation translates into a darker (lower) pixel value, then errors in the ability of the imaging plate to absorb radiation will appear as lighter (higher) pixel values. This is similarly evident in the overlapped region as the upper imaging plate partially blocks and absorbs some of the radiation and therefore the corresponding images on the lower image 502 are lighter in the overlapped region 506.

The higher quality pixel values from each pair of corresponding pixels are selected at 224 for use in the composite image.

Finally, after the upper and lower images are combined into a composite image, at 224, the composite image, at 226, is either presented on a graphical display, printed to a paper or photographic hard copy, or the composite image is digitally stored on a storage medium for later access and retrieval.

It is to be noted that the embodiments of the method as specifically disclosed herein are merely exemplary of the processing that may be performed in the acquisition of a composite image. It is to be understood that alternative embodiments, not specifically disclosed herein, are within the contemplated scope of the disclosure and that the disclosed methods may be performed in alternative orders, but for steps that have been disclosed as requiring any other specific steps as a precursor.

This written description uses examples to disclose various embodiments, including the best mode, and also to enable any person skilled in the art to make and use these embodiments. The patentable scope is defined by the claims may extend to include other examples not explicitly listed that occur to those skilled in the art. Such other examples are intended to be within the scope of the claims if they have structural elements that do not differ from the literal language of the claims, or if they include equivalent elements with insubstantial differences from the literal languages of the claims.

Various alternatives and embodiments are contemplated as being with in the scope of the following claims, particularly pointing out and distinctly claiming the subject matter of the present disclosure.

What is claimed is:

1. A medical imaging assembly comprising:
   a first imaging plate for acquiring a first medical image;
   a second imaging plate for acquiring a second medical image;
   a first carton disposed on the first imaging plate;
   a second carton disposed on the second imaging plate; and
   a container disposed about the first imaging plate and the second imaging plate, an interior of the container dimensioned to hold the first imaging plate and the second imaging plate together in an overlapping orientation within a predetermined overlapping alignment tolerance, and the container is further configured to be at least partially received within the mouth of a patient;
   wherein the first imaging plate and the second imaging plate are held within the predetermined alignment tolerance by friction and the first and second cartons enhance a friction fit between the first imaging plate, the second imaging plate, and the container.

2. The medical imaging assembly of claim 1, wherein each of the first imaging plate and the second imaging plate further comprise a phosphorous layer for absorbing x-ray radiation.

3. The medical imaging assembly of claim 1, further comprising a pouch of a fluid impervious construction configured to receive and hold the first imaging plate, second imaging plate, and container.

4. The medical imaging assembly of claim 1, wherein the predetermined overlapping alignment tolerance comprises a distance out of square between the first imaging plate and the second imaging plate.

5. The medical imaging assembly of claim 1, wherein the container is configured to receive and hold two imaging plates.

6. The medical imaging assembly of claim 1, wherein the first imaging plate and the second imaging plate are generally rectangular.

7. The medical imaging assembly of claim 1, wherein the container is generally rectangular.

8. The medical imaging assembly of claim 7, wherein the container comprises a closed end and an open end opposite the closed end, the open end configured to receive the first imaging plate and the second imaging plate.

9. The medical imaging assembly of claim 8, wherein the container comprises carbon fiber.

10. The medical imaging assembly of claim 7, wherein the container comprises cardboard.

11. A system for medical imaging, the system comprising:
a first imaging plate configured to acquire a first medical image;
a second imaging plate configured to acquire a second medical image;
a first carton disposed on the first imaging plate;
a second carton disposed on the second imaging plate;
a container disposed about the first imaging plate and the second imaging plate, an interior of the container dimensioned to hold the first imaging plate and the second imaging plate together in an overlapping orientation within a predetermined overlapping alignment tolerance, the first imaging plate and the second imaging plate are held within the predetermined alignment tolerance by friction and the first and second cartons enhance a friction fit between the first imaging plate, second imaging plate, and the container, and the container is further configured to be at least partially received within the mouth of a patient;
an image reader configured to convert the first medical image and the second medical image to a first digital medical image and a second digital medical image; and
a processor configured to receive the first and second digital medical images and create a composite image of the first and second digital images.

12. The system of claim 11, wherein the medical imaging is occlusal radiology, and the first and second imaging plates each comprise a phosphorous layer that records x-ray radiation exposure.

13. The system of claim 12, further comprising a first carton on the first imaging plate and a second carton on the second imaging plate, wherein the first and second cartons are configured to protect the first and second imaging plates.

14. The system of claim 13, further comprising a pouch configured to receive and hold the first imaging plate, the second imaging plate, and the container, and wherein the pouch is configured to be placed in a patient's mouth for acquisition of the first and second medical images.

15. The system for medical imaging of claim 11, further comprising a graphical display that displays the composite image.

16. The system for medical imaging of claim 11, further comprising a computer readable medium that receives and stores the composite image.

17. The system for medical imaging of claim 11, wherein the processor is configured to identify overlapping portions of the first digital medical image and the second digital medical image.

18. The system for medical imaging of claim 17, wherein the processor is configured to identify an alignment transformation that matches the overlapping portions of the first digital medical image and the second digital medical image.

19. The system for medical imaging of claim 18, wherein the processor is configured to align the first digital medical image and the second digital medical image based upon the identified alignment transformation.

20. The system for medical imaging of claim 18, wherein the alignment transformation comprises a spatial shift.

21. The medical imaging assembly of claim 1, wherein the interior of the container is further dimensioned to hold the first imaging plate in a first plane and further dimensioned to hold the second imaging plate in a second plane, the first plane being parallel to and different from the second plane.

22. The system of claim 11, wherein the interior of the container is further dimensioned to hold the first imaging plate in a first plane and further dimensioned to hold the second imaging plate in a second plane, the first plane being parallel to and different from the second plane.

23. A method of medical imaging, the method comprising:
providing a first imaging plate configured to acquire a first medical image;
providing a second imaging plate configured to acquire a second medical image;
providing a container disposed about the first imaging plate and the second imaging plate, the container having an interior with a dimension and configured to be at least partially received within the mouth of a patient; and
holding the first imaging plate and the second imaging plate in an overlapping orientation within a predetermined overlapping alignment tolerance due to the dimension of the interior of the container;
wherein the first medical image is a first intra-oral dental image and the second medical image is a second intra-oral dental image.

24. The method of claim 23, further comprising:
acquiring the first medical image with the first imaging plate;
acquiring the second medical image with the second imaging plate;
converting the first medical image to a first digital medical image with an image reader;
converting the second medical image to a second digital medical image with the image reader; and
creating a composite image of the first and second digital images with a processor.

25. The method of claim 23, further comprising, providing a pouch configured to receive and hold the first imaging plate, the second imaging plate, and the container, wherein the pouch is configured to be placed in a patient's mouth.

26. The method of claim 23 further comprising:
holding the first imaging plate in a first plane due to the dimension of the interior of the container; and
holding the second imaging plate in a second plane due the dimension of the interior of the container;
wherein the first plane is different from and parallel to the second plane.

27. The method of claim 23 wherein the first imaging plate and the second imaging plate are held within the predetermined alignment tolerance by friction.

28. The method of claim 27 further comprising:
providing a first carton disposed on the first imaging plate; and
providing a second carton disposed on the second imaging plate.

29. The method of claim 28, wherein the first and second cartons enhance a friction fit between the first imaging plate and the second imaging plate.

30. The method of claim 23 further comprising:
providing a first carton disposed on the first imaging plate; and
providing a second carton disposed on the second imaging plate.

31. The medical imaging assembly of claim 1, wherein the first medical image is a first intra-oral dental image and the second medical image is a second intra-oral dental image.

32. The system for medical imaging of claim 11, wherein the first medical image is a first intra-oral dental image and the second medical image is a second intra-oral dental image.

33. A system for medical imaging, the system comprising:
- a first imaging plate configured to acquire a first medical image;
- a second imaging plate configured to acquire a second medical image;
- a container disposed about the first imaging plate and the second imaging plate, an interior of the container dimensioned to hold the first imaging plate and the second imaging plate together in an overlapping orientation within a predetermined overlapping alignment tolerance, and the container is further configured to be at least partially received within the mouth of a patient;
- an image reader configured to convert the first medical image and the second medical image to a first digital medical image and a second digital medical image; and
- a processor configured to receive the first and second digital medical images and create a composite image of the first and second digital images;
- wherein the first medical image is a first intra-oral dental image and the second medical image is a second intra-oral dental image.

34. The system for medical imaging of claim 33, further comprising
- a first carton disposed on the first imaging plate; and
- a second carton disposed on the second imaging plate.

35. The system for medical imaging of claim 33, wherein the first imaging plate and the second imaging plate are held within the predetermined alignment tolerance by friction.

36. The system for medical imaging of claim 35, further comprising:
- a first carton disposed on the first imaging plate; and
- a second carton disposed on the second imaging plate.

* * * * *